United States Patent [19]

Gutman

[11] 4,006,154
[45] Feb. 1, 1977

[54] HETEROCYCLIC SUBSTITUTED THIO AND SULFONYL GLYOXYLINITRILEOXIME PHOSPHATES AND PHOSPHONATES

[75] Inventor: Arnold D. Gutman, Berkeley, Calif.

[73] Assignee: Stauffer Chemical Company, Westport, Conn.

[22] Filed: Aug. 18, 1975

[21] Appl. No.: 605,587

Related U.S. Application Data

[62] Division of Ser. No. 222,368, Jan. 31, 1972, Pat. No. 3,931,358.

[52] U.S. Cl. .................. 260/302 E; 260/306.6 R; 260/309.2
[51] Int. Cl.² ............ C07D 277/74; C07D 277/36; C07D 235/28
[58] Field of Search ............. 260/302 E, 306.6 R, 260/309.2

[56] References Cited

UNITED STATES PATENTS 3,931,358   1/1976   Gutman .................. 260/302 E

*Primary Examiner*—R. Gallagher
*Attorney, Agent, or Firm*—Harry A. Pacini

[57] ABSTRACT

Compounds of the formula

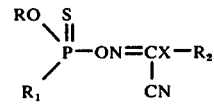

in which R is lower alkyl; $R_1$ is lower alkyl or lower alkoxy; X is thio or sulfonyl; $R_2$ is alkyl, benzothiazol-2-yl, benzyl, naphthyl, benzimidazol-2-yl, thiazol-2-yl, phenyl or substituted phenyl wherein said substituents are chloro, bromo, methyl or methoxy and the use of these compounds as insecticides.

11 Claims, No Drawings

HETEROCYCLIC SUBSTITUTED THIO AND SULFONYL GLYOXYLINITRILEOXIME PHOSPHATES AND PHOSPHONATES

This is a division of application Ser. No. 222,368 filed Jan. 31, 1972, now U.S. Pat. No. 3,931,358 issued Jan. 6, 1976.

This invention relates to certain novel phosphorus-containing chemical compounds and their use as insecticides. More particularly, the compounds of this invention are certain substituted thio and sulfonyl glyoxylnitrileoxime phosphates and phosphonates. The compounds find utility as insecticides.

The compounds of this invention that are useful as insecticides are those having the formula

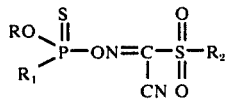

in which R is lower alkyl having 1 to 4 carbon atoms, inclusive; $R_1$ is selected from the group consisting of lower alkyl having 1 to 4 carbon atoms, inclusive, and lower alkoxy having 1 to 4 carbon atoms, inclusive; X is selected from the group consisting of thio and sulfonyl; $R_2$ is selected from the group consisting of alkyl having 1 to 6 carbon atoms, inclusive, benzathiazol-2yl, benzyl, naphthyl, benzimedazol-2-yl, thiazol-2-yl, phenyl or substituted phenyl wherein said substituents are selected from the group consisting of chloro, bromo, methyl and methoxy.

Representative of R and $R_1$ as lower alkyl having 1 to 4 carbon atoms, inclusive, are straight and branched chain members, such as, methyl, ethyl, n-propyl, isopropyl, n-butyl, isobutyl, tertiary-butyl; for $R_2$ as alkyl having 1 to 6 carbon atoms, inclusive, methyl, ethyl, n-propyl, isopropyl, n-butyl, isobutyl, tertiary-butyl, n-pentyl, isopentyl, n-hexyl, isohexyl and the like.

The compounds having the formula

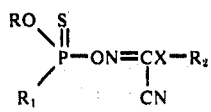

in which R, $R_1$ and $R_2$ are as defined above, can be conveniently prepared by the following reactions:

(1) 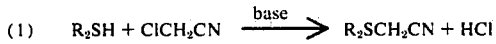

(2) 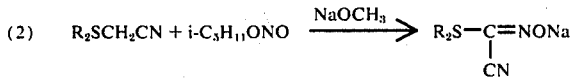

(3) 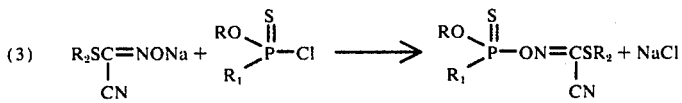

The compounds having the formula

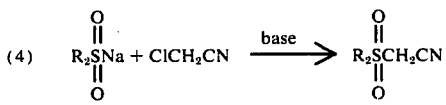

in which R, $R_1$ and $R_2$ are as defined above can be conveniently prepared by the following reactions:

(4) 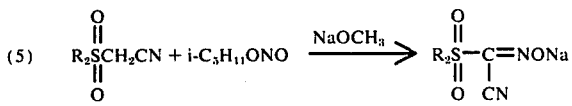

(5) 

(6) 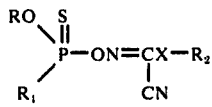

The compounds of the instant invention can be prepared by the reactions depicted in the above equations. Selection of time, temperature and solvents can be made within wide limitations. Once the equations and reactants are known, the specific procedures can be varied and modified to accommodate and facilitate the reactions. The intermediate from equation (1), i.e., the acetonitrile, can be isolated or reacted in the same or different solvent, or the reaction can be carried through to completion without isolation.

To facilitate reactions (1) and (4), a non-reactive acid acceptor is used as a catalyst. In the following examples, specific materials are use as the base, however, other non-reactive acid acceptors would be acceptable.

Reactions (2) and (5) represent the reaction of the corresponding acetonitrile with an alkyl nitrile in the presence of a strong base, such as sodium methoxide or potassium t-butoxide to produce the sodium salt of an alkyl thio, or sulfonyl. Reactions (3) and (6) represent the reaction of the sodium salt with an appropriate substituted phosphoro or phosphono thiochloridate.

Reactions (3) and (6) are preferably carried out in the presence of an inert solvent such as ethanol, tetrahydrofuran, benzene, acetone and the like.

The compounds of the present invention and their preparation are more particularly illustrated by the following examples. Following the examples is a table of compounds which are prepared according to the procedures described herein.

EXAMPLE I

Preparation of Intermediate A: 2-Cyanomethylthiobenzothiazole. In a 1 liter flask were combined 33.4 g. (0.2 mole) of 2-mercaptobenzothiazole and 22.4 g. (0.2 mole) of potassium t-butoxide with 300 ml. of tetrahydrofuran. The reaction mass was stirred at room temperature for 15 minutes. Chloroacetonitrile, 16 g. (0.2 mole) was added and the resulting mixture was stirred at room temperature for 1 hour. The mixture was then poured into 400 ml. of benzene and was washed with three 250 ml. portions of water. The benzene phase was dried with anhydrous magnesium sulfate. The solvent was evaporated. There was obtained a yield of 37.2 g. of the title compound, m.p. 75°–77° C.

Preparation of Intermediate B: Benzothiazolo-2-mercaptoglyoxylonitrileoxime sodium salt. In a 500 ml. flask was combined 20.6 g. (0.1 mole) of 2-cyano methylthiobenzothiazole, 11.7 g. (0.1 mole) of iso-amylnitrite, 100 ml. of methanol, and 100 ml. of tetrahydrofuran. The mixture was stirred at room temperature until a clear solution was obtained and then cooled to 10° C. with an ice bath. A 25% sodium methoxide solution in methanol, 21.6 g. (0.1 mole), was added at such a rate that the temperature did not exceed 10° C. After the addition was complete, the reaction mass was stirred at room temperature for 1 hour. The reaction mass was stripped of all volatiles under a vacuum. The solid residue was titurated with two 200 ml. portions of diethylether and dried. There was obtained a yield of 16.6 g. of the title compound, m.p. 200° C. dec.

Preparation of Benzothiazolo-2-mercaptoglyoxylonitrileoxime-0,0-diethylphosphorothioate. In a 250 ml. flask were combined 7.3 g. (0.03 mole) of benzothiazolo-2-mercaptoglyoxylonitrileoxime sodium salt, 5.6 g. (0.03 mole) of diethylphosphorothio chloridate and 150 ml. of tetrahydrofuran. The reaction mass was stirred and heated under reflux for 1 hour, then cooled and poured into 300 ml. of benzene. The benzene mixture was washed with three 200 ml. portions of water, dried with anhydrous magnesium sulfate and treated with activated carbon. The solvent was evaporated in vacuo. There was obtained a yield of 4.3 g. of the title compound $n_D^{30} = 1.5800$.

EXAMPLE II

Preparation of Intermediate C: Methylthioacetonitrile

In a 500 ml. flask were combined 50.5 g. (0.5 mole) of triethylamine and 300 ml. of benzene. As the solution was stirred and cooled externally to 10° C. with an ice bath, 30 g. (0.625 mole) of methyl mercaptan gas was introduced. The gas inlet tube was replaced with a dropping funnel, and 37.8 g. (0.5 mole) of chloroacetonitrile was added over a period of 15 minutes. After the addition was complete, the reaction mass was stirred at 40° C. for 1 hour. The mixture was then washed in turn with 250 ml. of dilute hydrochloric acid and two 200 ml. portions of water. The benzene phase was dried with anhydrous magnesium sulfate and the solvent evaporated. There was obtained a yield of 33.4 g. of the title compound, $n_D^{30} = 1.5002$.

Preparation of Intermediate D: Methylthioglyoxylonitrileoxime sodium salt. In a 500 ml. flask was combined 33.4 g. (o.384 mole) of methylthioacetonitrile, 46.8 g. (0.4 mole) of iso-amylnitrite, 150 ml. of methanol, and 150 ml. of tetrahydrofuran. The mixture was stirred at room temperature until a clear solution was obtained and then cooled to 10° C. with an ice bath. 86.5 g. (0.4 mole) of a 25% sodium methoxide solution in methanol was added at such a rate that the temperature did not exceed 10° C. After the addition was complete, the reaction mass was stirred at room temperature for 1 hour. The reaction mass was then stripped of all volatiles. The solid residue was titurated with two 200 ml. portions of diethyl ether and dried. There was obtained a yield of 51.8 g. of the title compound, hygroscopic, white solid.

Preparation of Methylthioglyoxylonitrileoxime-O,O-diethyl phosphorothioate

In the same manner as Example I, 6.9 g. (0.05 mole) of methylthioglyoxylonitrileoxime sodium salt, 94 g. (0.05 mole) of diethylphosphorothio chloridate and 200 ml. of ethanol were combined to yield 10.0 g. of the title compound, $n_D^{30} = 1.4932$.

EXAMPLE III

Preparation of Methylthioglyoxylonitrileoxime-O,0-dimethylphosphorothioate

In the same manner as Example I, 6.9 g. (0.05 mole) of methylthioglyoxylonitrileoxime sodium salt, 8.09 g. (0.05 mole) of dimethylphosphorothio dichloridate, and 250 ml. of methanol were combined to yield 7.8 g. of the title compound, $n_D^{30} = 1.5050$.

EXAMPLE IV

Preparation of Intermediate E: Phenylsulfonylacetonitrile

Benzene sulfinic acid sodium salt, 49.2 g. (0.3 mole) was combined with 400 ml. of dimethyl formamide in a 1 liter flask. The mixture was stirred at 40° C. Chloroacetonitrile, 22.5 g. (0.3 mole) was added over a period of 5 minutes. The resulting mixture was stirred and heated at 40°–45° C. for 2 hours. The reaction mass was then poured into 600 ml. of water, and the solid insoluble product was collected by suction filtration and dried. There was obtained a yield of 29.8 g. of the title compound, m.p. 111°–112° C.

Preparation of Intermediate F: Phenylsulfonylglyoxylonitrileoxime sodium salt

In the same manner as Example I, Intermediate B, 29.8 g. (0.065 mole) of phenylsulfonylacetonitrile, 19.9 g. (0.17 mole) of iso-amylnitrile, and 36.7 g. (0.17 mole) of 25% sodium methoxide solution in methanol were combined in 300 ml. of tetrahydrofuran to yield 37.3 g. of the title compound, m.p. 240° C. dec.

Preparation of Phenylsulfonylglyoxylonitrileoxime-O,O-diethyl phosphorothioate.

In the same manner as Example I, 4.8 g. (0.02 mole) of phenylsulfonylglyoxylonitrileoxime sodium salt and 3.7 g. (0.02 mole) of diethylphosphorothiochloridate were combined in 200 ml. of ethanol to yield 6.6 g. of the title compound, $n_D^{30} = 1.5134$.

The following is a table of certain selected compounds that can be prepared according to the procedures described herein. Compound numbers are assigned to each compound and are used throughout the remainder of the application.

TABLE I $$\begin{array}{c} RO \\ \diagdown \\ R_1 \end{array} \overset{S}{\underset{\|}{P}} - ON = \underset{CN}{\overset{|}{C}} - X - R_2$$

| COMPOUND NUMBER | R | $R_1$ | X | $R_2$ | $n_D^{30}$ or m.p. °C. |
|---|---|---|---|---|---|
| 1 | Et | OEt | S | 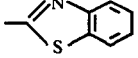 | 1.5800 |
| 2 | Me | OMe | S | 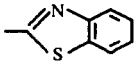 | 1.5980 |
| 3 | Et | OEt | S | 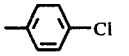 | 1.5417 |
| 4 | Me | OMe | S |  | 1.5706 |
| 5 | Et | OEt | S | $CH_3$ | 1.4932 |
| 6 | Me | OMe | S | $CH_3$ | 1.5050 |
| 7 | Me | OMe | S | tert.-$C_4H_9$ | 1.4920 |
| 8 | Et | OEt | S | tert.-$C_4H_9$ | 1.4940 |
| 9 | Et | OEt | $SO_2$ |  | 1.5134 |
| 10 | Me | OMe | $SO_2$ | 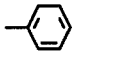 | 1.5205 |
| 11 | Et | OEt | S | 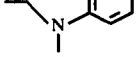 | Dark oil |
| 12 | Et | OEt | $SO_2$ | 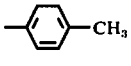 | 1.5215 |
| 13 | Me | OMe | $SO_2$ | 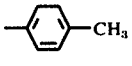 | 1.5457 |
| 14 | Et | OEt | S | 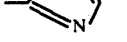 | 1.4898 |
| 15 | Me | OMe | S | 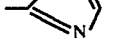 | 1.5087 |
| 16 | Et | Et | S | 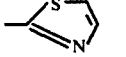 | 1.4930 |
| 17 | Et | OEt | S | i-$C_5H_{11}$ | 1.4918 |
| 18 | Me | OMe | S | i-$C_5H_{11}$ | 1.4963 |
| 19 | Et | Et | S | i-$C_5H_{11}$ | 1.5060 |
| 20 | Et | OEt | S | i-$C_4H_9$ | 1.4828 |
| 21 | Me | OMe | S | i-$C_4H_9$ | 1.4958 |
| 22 | Et | Et | S | i-$C_4H_9$ | 1.4973 |
| 23 | Et | OEt | S | Et | 1.4983 |
| 24 | Me | OMe | S | Et | 1.5041 |
| 25 | Et | Et | S | Et | 1.5198 |
| 26 | Et | OEt | S | i-$C_3H_7$ | 1.4930 |
| 27 | Me | OMe | S | i-$C_3H_7$ | 1.5029 |
| 28 | Et | Et | S | i-$C_3H_7$ | 1.5065 |
| 29 | Et | OEt | $SO_2$ | 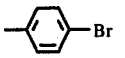 | 1.5360 |
| 30 | Me | OMe | $SO_2$ | 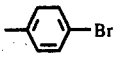 | 1.5500 |
| 31 | Et | OEt | S |  | 1.5390 |
| 32 | Me | OMe | S |  | 1.5570 |
| 33 | Et | Et | S |  | 1.5530 |
| 34 | Et | OEt | $SO_2$ |  | 1.5465 |
| 35 | Me | OMe | $SO_2$ |  | 1.5342 |
| 36 | Et | Et | $SO_2$ |  | 1.5623 |
| 37 | Et | OEt | $SO_2$ |  | 1.5201 |
| 38 | Et | Et | $SO_2$ |  | 1.5462 |

INSECTICIDAL EVALUATION TESTS

The term "insect" is used herein in its broad common usage to include spiders, mites, ticks and like pests which are not in the strict biological sense classified as insects. The term "insect" is used to refer not only to those small invertebrate animals belonging moistly to the class Insecta, comprising six-legged usually winged forms, as beetles, bugs, bees, flies, and so forth, but also to other allied classes of arthropods whose members are wingless and usually have more than six legs, as spiders, mites, ticks, centipedes, and wood lice.

The following insect species were used in evaluation tests for insecticidal activity:

1. Housefly (HF) — *Musca domestica* (Linn.)
2. Lygus Bug (LB) — *Lygus hesperus* (Knight)
3. German Cockroach (GR) — *Blatella germanica* (Linn.)
4. Bean Aphid (BA) — *Aphis fabae* Scop.
5. Beet Armyworm (BAW) — *Spodoptera exigua* (Hubner)
6. Mosquito (MOS) — *Culex pipiens quinquefasciates*

The housefly (HF) was used in the following film residue, evaluation tests of selected compounds as insecticides by the following procedure. A stock solution containing 100 μg/ml. of the toxicant in an appropriate solvent was prepared. Aliquots of this solution were combined with 1 milliliter of an acetone-peanut oil solution in a glass petri dish and allowed to dry. The aliquots were there to achieve desired toxicant concentration ranging from 100 μg/per petri dish to that at which 50% mortality was attained. The petri dishes were placed in a circular cardboard cage, closed on the bottom with cellophane and covered on top with cloth netting. Twenty-five female houseflies, three to five days old, were introduced into the cage and the percent mortality was recorded after 48 hours. The LD-50 values are expressed in terms of μg per 25 female flies. The results of this insecticidal evaluation test are given in Table II under "HF".

In the insecticidal test employing German Cockroach, 10 one-month-old nymphs are placed into a circular cardboard cage sealed on one end with cellophane and covered by cloth netting on the other. Aliquots of the toxicant, dissolved in an appropriate solvent, are diluted in water to which has been added 0.0002% of a conventional wetting agent such as polyoxyethylene sorbitan monolaurate ether of alkylated phenols blended with organic sulfonate (Sponto 221). Test concentrations range from 0.1% to that at which 50% mortality is obtained. Each of these aqueous suspensions are sprayed onto the insects, through the cloth netting, by means of a hand spray gun. Percent mortality is recorded after 72 hours and the LD-50 values are expressed as percent of toxicant in the aqueous spray. These values are reported under the Column "GR" in Table II.

In the insecticidal test employing Beet Armyworm, test solutions were prepared in the same manner and at the same concentrations as those used for German Cockroach test. Sections of Romaine lettuce (*Latuca sativa*) were utilized as the host plant. The lettuce leaves were immersed in the test solution for 10–15 seconds and placed on a wire screen to dry. The dried leaf was placed on a moistened piece of filter paper in a petri dish and infested with five third-instar larvae. Mortality of the larvae was recorded after 72 hours. The LD-50 values are expressed as percent active ingredient in the aqueous suspensions. These values are reported under Column "BAW" in Table II.

In the lygus Bug test, ten to twenty-five two-week old nymphs of lygus bug were placed in separate circular cardboard cages sealed on one end with cellophane and covered by a cloth netting on the other. Aliquots of the toxicants, dissolved in an appropriate solvent, were diluted in water containing 0.002% of a wetting agent, Sponto 221 (polyoxyether of alkylated phenols blended with organic sulfonates). Test concentrations ranged from 0.05% downward to that at which 50% mortality was obtained. Each of the aqueous suspensions of the candidate compounds were sprayed onto the insect through the cloth netting by means of a hand spray gun. Percent mortality in each case recorded after 24 and 72 hours counts were made to determine living and dead insects. The LD-50 values expressed as per cent of toxicant in the aqueous spray were calculated and recorded. These values are reported under Column "LB" in Table II.

The insect species black bean aphid (BA) *Aphis fabae* (Scop.) was also employed in the test for insecticidal activity. Young nasturtium (Tropaeolum sp.) plants, approximately 2 to 3 inches tall, were used as the host plants for the bean aphid. The host plant was infested with approximately 50–75 of the aphids. The test chemical was dissolved in acetone, added to water which contained a small amount of Sponto 221, an emulsifying agent. The solution was applied as a spray to the infested plants. Concentrations ranged from 0.05 percent downward until and LD-50 value was achieved. These results are given in Table II under the Column "BA".

Mosquito Bioassay

One hundred milliliters of an aqueous solution of the candidate compound, at an initial concentration of 0.5 p.p.m., are placed in a 6 ounce wax paper cup. Ten late third or early fourth instar larvae of the mosquito *Culex pipiens quinquefasciates* are placed in each cup and the cups are stored at 70° F. for three days. At the end of this time, mortality counts are made. Compounds which are active at 0.5 p.p.m. are retested at progressively lower concentrations until an $LD_{50}$ value is determined. These results are given in Table II under the Column "MOS".

TABLE II

| COMPOUND NUMBER | HF $\mu g/25° +$ | (LD-50 VALUES) INSECTICIDE TESTS | | | | |
|---|---|---|---|---|---|---|
| | | GR % | LB % | BA % | BAW % | MOS ppm. |
| 1 | 15 | .05 | .001 | .003 | .03 | .08 |
| 2 | >100 | — | — | >.05 | — | — |
| 3 | >100 | — | — | >.05 | — | — |
| 4 | >100 | — | — | >.05 | — | — |
| 5 | 30 | .08 | .005 | .01 | .03 | .08 |
| 6 | 15 | >.1 | .005 | .01 | .03 | .3 |
| 7 | 100 | >.1 | .03 | >.05 | .1 | >.5 |
| 8 | 30 | .03 | .001 | .003 | .003 | .03 |
| 9 | 30 | .1 | .03 | .03 | — | .5 |
| 10 | 40 | >.1 | .03 | .05 | — | >.5 |
| 11 | 7 | .03 | .008 | .008 | .03 | .03 |
| 12 | 5 | .03 | .003 | .003 | .05 | .3 |
| 13 | 30 | >.1 | .01 | .03 | — | .5 |
| 14 | 30 | .03 | .008 | .03 | — | >.5 |
| 15 | 30 | >.1 | .05 | >.05 | — | >.5 |
| 16 | 30 | .03 | .003 | .005 | — | >.5 |
| 17 | 45 | .1 | .03 | .03 | — | .05 |
| 18 | 80 | .1 | .05 | .003 | — | .08 |
| 19 | 30 | .03 | .008 | .003 | — | .08 |
| 20 | 30 | .05 | .008 | .003 | — | .03 |
| 21 | 30 | .05 | .005 | .005 | — | .03 |
| 22 | 30 | .08 | .008 | .01 | .08 | .5 |
| 23 | 30 | .03 | .008 | .005 | .01 | .03 |
| 24 | 30 | .1 | .005 | .008 | — | .3 |
| 25 | 9 | .03 | .005 | .003 | .03 | .03 |
| 26 | 40 | .05 | .03 | .03 | .03 | — |
| 27 | 50 | >.1 | .005 | .03 | — | .03 |
| 28 | 10 | .03 | .005 | .008 | .03 | .03 |
| 29 | 30 | .03 | .005 | .03 | .08 | .3 |
| 30 | 30 | >.1 | .03 | .03 | >.1 | >.5 |
| 31 | 30 | .1 | >.05 | .003 | .01 | .03 |

TABLE II-continued

| COMPOUND NUMBER | HF μg/25°+ | (LD-50 VALUES) INSECTICIDE TESTS | | | | MOS ppm. |
|---|---|---|---|---|---|---|
| | | GR % | LB % | BA % | BAW % | |
| 32 | 50 | >.1 | .05 | .005 | >.1 | .03 |
| 33 | 30 | .008 | .01 | .003 | .01 | .03 |
| 34 | 30 | .05 | .03 | .03 | >.1 | >.5 |
| 35 | 10 | >.1 | >.05 | >.05 | >.1 | >.5 |
| 36 | 30 | .1 | .01 | .03 | >.1 | >.5 |
| 37 | 50 | >.1 | .03 | .03 | >.1 | >.5 |
| 38 | 40 | >.1 | .03 | .03 | >.1 | >.5 |

(—) indicates not tested.

As those in the art are well aware, various techniques are available for incorporating the active component or toxicant in suitable pesticidal compositions. Thus, the pesticidal compositions can be conveniently prepared in the form of liquids or solids, the latter preferably as homogeneous free-flowing dusts commonly formulated by admixing the active component with finely divided solids or carriers as exemplified by talc, natural clays, diatomaceous earth, various flours such as walnut shell, wheat, soya bean, cottonseed and so forth.

Liquid compositions are also useful and normally comprise a dispersion of the toxicant in a liquid media although it may be convenient to dissolve the toxicant directly in a solvent such as kerosene, fuel oil, xylene, alkylated naphthalenes or the like and use such organic solutions directly. However, the more common procedures is to employ dispersions of the toxicant in an aqueous medium and such compositions may be produced by forming a concentrated solution of the toxicant in a suitable organic solvent followed by dispersion in water, usually with the aid of surface active agents. The latter, which may be anionic, cationic or nonionic types, are exemplified by sodium stearate, potassium oleate and other alkaline metal soaps and detergents such as sodium lauryl sulfate, sodium naphthalene sulfonate, sodium alkyl naphthalene sulfonate, methyl cellulose, fatty alcohol ethers, polyglycol fatty acid esters, and other polyoxyethylene surface active agents. The proportion of these agents commonly comprises 1–15% by weight of the pesticidal compositions although the proportion is not critical and may be varied to suit any particular situation.

What is claimed is:
1. A compound of the formula

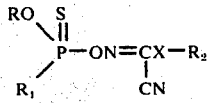

in which R is lower alkyl having 1 to 4 carbon atoms, inclusive; $R_1$ is selected from the group consisting of lower alkyl having 1 to 4 carbon atoms, inclusive, and lower alkoxy having 1 to 4 carbon atoms, inclusive; X is selected from the group consisting of thio and sulfonyl; $R_2$ is selected from the group consisting of benzothiazol-2-yl, benzimidazol-2-yl, and thiazol-2-yl.

2. The compound according to claim 1 in which R is lower alkyl, $R_1$ is lower alkoxy, X is thio and $R_2$ is benzothiazol-2-yl.

3. The compound according to claim 2 in which R is ethyl and $R_1$ is ethoxy.

4. The compound according to claim 2 in which R is methyl and $R_1$ is methoxy.

5. The compound according to claim 1 in which R is alkyl, $R_1$ is alkoxy, X is thio and $R_2$ is benzimidazol-2-yl.

6. The compound according to claim 5 in which R is ethyl and $R_1$ is ethoxy.

7. The compound according to claim 1 in which R is lower alkyl, $R_1$ is lower alkoxy, X is thio and $R_2$ is thiazol-2-yl.

8. The compound according to claim 7 in which R is ethyl and $R_1$ is ethoxy.

9. The compound according to claim 7 in which R is methyl and $R_1$ is methoxy.

10. The compound according to claim 1 in which R is lower alkyl, $R_1$ is lower alkyl, X is thio and $R_2$ is thiazol-2-yl.

11. The compound according to claim 10 in which R is ethyl and $R_1$ is ethyl.

* * * * *